US007229978B2

(12) United States Patent
Bonneville et al.

(10) Patent No.: US 7,229,978 B2
(45) Date of Patent: Jun. 12, 2007

(54) PROCESS FOR PREPARING WATER SOLUBLE PHOSPHONOOXYMETHYL DERIVATIVES OF ALCOHOL AND PHENOL

(75) Inventors: George Bonneville, Baltimore, MD (US); Greg Delahanty, Baltimore, MD (US); Andrew J. Walz, Baltimore, MD (US)

(73) Assignee: MGI GP, Inc., Baltimore, MD (US)

( * ) Notice: Subject to any disclaimer, the term of this patent is extended or adjusted under 35 U.S.C. 154(b) by 0 days.

(21) Appl. No.: 10/498,013

(22) PCT Filed: Dec. 20, 2002

(86) PCT No.: PCT/US02/40748

§ 371 (c)(1),
(2), (4) Date: Dec. 21, 2004

(87) PCT Pub. No.: WO03/059255

PCT Pub. Date: Jul. 24, 2003

(65) Prior Publication Data

US 2005/0124787 A1     Jun. 9, 2005

Related U.S. Application Data

(60) Provisional application No. 60/341,867, filed on Dec. 21, 2001.

(51) Int. Cl.
*A61K 31/66* (2006.01)
(52) U.S. Cl. .................. 514/75; 514/130; 514/458; 558/87; 558/89; 558/177
(58) Field of Classification Search .................. 514/75, 514/130, 458; 558/87, 89, 177
See application file for complete search history.

(56) References Cited

U.S. PATENT DOCUMENTS 2,833,827 A    5/1958   Hahn et al.
6,204,257 B1   3/2001   Stella et al.

FOREIGN PATENT DOCUMENTS

GB           814278           6/1959

OTHER PUBLICATIONS

Yu et al, "Phenol Conversion and Dimeric Intermediates in Horseradish Peroxidase-Catalyzed Phenol Removal from Water", Environ. Sci. Technol., 1994, vol. 28, p. 2154-2160.
Trapani et al, "Propfol Analogues. Synthesis, Relationships between Structure and Affinity at $GABA_A$ Receptor in Rat Brain, and Differential Electrophysiological Profile at Recombinant Human $GABA_A$ Receptors", J. Med. Chem., 1998, vol. 41, p. 1846-1854.
Tashiro et al., "Oxidative Coupling Reaction of 2-Halophenols with $K_3Fe(CN)_6$ in Benzene Solution", Heterocycles, 1983, vol. 20, No. 4, p. 653-660.
Sowa et al, "Organic Reactions with Boron Fluoride. II. The rearrangement of Alkyl Phenyl Ethers", University of Notre Dame, May 1932, p. 2019-2021.
Siuzdak et al., "Multiphoton Ionization of Phenol in Nonaqueous Solutions: Characterization of the Cation and Ion-Molecule Chemistry", J. Phys. Chem., 1991, vol. 95, p. 5186-5190.
Servis et al., "Conformational Analysis Using Lanthanide Shift Reagents. Determination of Alkyl Group Conformations in 2-Alkyl-4-*tert*-butycyclohexanones", Journal of the American Chemical Society, vol. 97, No. 1, Jan. 8, 1975, p. 80-88.
Sendra et al., "Volatile Phenolic Constituents of Spanish Origanum (*Coridothymus capitatus*) Essential Oil", Phytochemistry, 1980, vol. 19, p. 1513-1517.
Rosevear et al., "Preparation of Some 2-(2' *H*-Benzotriazol-2'-yl)phenol Ultraviolet Absorbers: Application of the Transalkylation Reaction", Aust. J. Chem., 1985, vol. 38, p. 1163-1176.
Petranek et al., "Two-Step Reduction of Alkylated Diphenoquinones in Acetonitrile", Collection Czechoslov. Chem. Commun., 1970, vol. 35, p. 2571-2581.
Nishino et al., "Choice of Manganese(III) Complexes for the Synthesis of 4,4'-Biphenyldiols and 4,4'-Diphenoquiones", Bull. Chem. Soc. Jpn., 1992, vol. 65, p. 620-622.
Nilsson et al., "3-Heteroaryl-Substituted Quinuclidin-3-ol and Quinuclidin-2-ene Derivatives as Muscarinic Antagonists. Synthesis and Structure—Activity Relationships", J. Med. Chem., 1995, vol. 38, p. 473-187.

(Continued)

*Primary Examiner*—David Lukton
(74) *Attorney, Agent, or Firm*—Banner & Witcoff, Ltd.

(57) ABSTRACT

A process for making water-soluble phosphonooxymethyl ethers of hindered alcohol and phenol containing pharmaceuticals, such as camptothecin, propofol, etoposide, Vitamin E and Cyclosporin A. In particular, the process for preparing water-soluble phosphonooxymethyl derivatives comprises the steps of Formula (i) and Formula (ii); R—OH represents an alcohol- or phenol-containing drug, n represents an integer of 1 or 2, $R^1$ is hydrogen, an alkali metal ion, or a pharmaceutically acceptable cation, and $R^2$ is hydrogen, an alkali metal ion, or a pharmaceutically acceptable cation

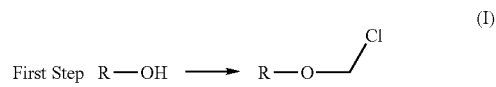

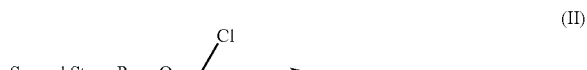

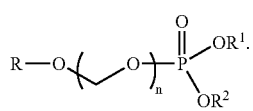

26 Claims, No Drawings

OTHER PUBLICATIONS

Neuworth et al., "Synthesis and Hypocholesterolemic Activity of Alkylidenedithio Bisphenols", Journal of Medicinal Chemistry, 1970, vol. 13, No. 4, p. 722-725.

Omura, "Silver Ion-Mediated Coupling of 4-Bromo-2,6-di-*tert*-butylcycohexa-2,5-dienone with Phenols", J. Org. Chem., 1998, vol. 63,p. 10031-10034.

Middleton, "Hexafluoroacetone Azine. Reaction with Cyclohexane by a Radical Double Chain Mechanism", Journal of the American Chemical Society, 1971, vol. 13, No. 2, p. 423-425.

Mandal et al., "Novel *tert*-Butyl Migration in Copper-Mediated Phenol *Ortho*-Oxygenation Implicates a Mechanism Involving Conversion of a 6-Hydroperoxy-2,4-cyclohexadienone Directly to an o-Quinone", J. Org. Chem., 2000, vol. 65, p. 4804-4809.

Krise et al, "Novel Prodrug Approach for Tertiary Amines: Synthesis and Preliminary Evaluation of *N*-Phosphonooxymethyl Prodrugs", J. Med. Chem., 1999, vol. 42, p. 3094-3100.

James et al., "Synthesis, Biological Evaluation, and Preliminary Structure-Activity Considerations of a Series of Alkylphenols as Intravenous Anesthetic Agents", J. Med. Chem., 1980, vol. 23, p. 1350-1357.

Klemm et al., "Alumina-Catalyzed Reactions of Hydroxyarenes and Hydroaromatic Ketones. A. Reaction of Phenol with 1-Propanol", J. Org. Chem., 1980, vol. 45, p. 4320-4326.

Hay, "p.p'-Biphenols", The Journal of Organic Chemistry, 1968, p. 1160-1161.

Hayami et al., "Sn2 Reactions in Dipolar Aprotic Solvents. Chlorine Isotopic Exchange Reactions of 2-Arylethyl Chlorides, Chloromethyl Aryl Ethers, and Chloromethyl Aryl Sulfides in Acetonitrile", Bulletin of the Chemical Society of Japan, Nov. 1971, vol. 44, p. 3091-3095.

Harden et al., "The Condensation of Certain Phenols with Some Aliphatic Aldehydes", Johns Hopkins University, Nov. 1932, p. 4325-4334.

Granoth et al., "Chemical Consequences of Hydride Addition to Aromatic Olefins", J. Org. Chem., 1976, vol. 41, No. 23, p. 3682-3686.

Gomberg et al., "The Condensation of Carbon Tetrachloride and Phenol: Aurin", University of Michigan, Jan. 1925, vol. 47, p. 198-211.

Evans et al., "Regioselective and Enantiospecific Rhodium-Catalyzed Intermolecular Allylic Etherification with Ortho-Substituted Phenols", J. Am. Chem. Soc., 2000, vol. 122, p. 5012-5013.

Dewar et al., "Acid-catalysed Rearrangements of Alkyl Aryl Ethers. Part IV. Rearrangement of Alkyl Tolyl Ethers by Aluminium Chloride", Shirley Institute Manchester, 1960, p. 959-963.

Dasgupta et al., "Mathematical Models to Calculate Fosphenytoin Concentrations in the Presence of Phenytoin Using Phenytoin Immunoassays and Alkaline Phosphatase", www.ajcp.com/Vol_113/JAN2000/Articles/.../dasgup01.htm, Aug. 29, 2001.

Coffield et al., "Some reactions of 2,6-Dialkylphenols", Detroit Laboratories of the Ethyl Corp., Sep. 20, 1957, vol. 79, p. 5019-5023.

"Cerebyx® (Fosphenytoin Sodium Injection)", Product Description, Warner-Lambert Co., Revised May 1999.

Blank et al., "Thyromimetics. VII. Isopropyl Analogs of Thyroid Hormones", Smith Kline and French Laboratories, Philadelphia, PA, Jul. 1967, vol. 10, p. 653-656.

Baik, et al., "NBS-Promoted Reactions of Symmetrically Hindered Methylphenols via *p*-Benzoquinone Methide", J. Org. Chem., 2000, vol. 65, p. 108-115.

Baik et al., "LiAlH$_4$ Promoted Reductive Deoxygenation of Hydroxybenzyl Alcohols *via* Benzoquinone Methide Intermediates", Tetrahedron Letters, 1998, vol. 39, p. 8125-8128.

Armstrong et al., "The Role of Stereoelectronic Factors in the Oxidation of Phenols", Tetrahedron Letters, 1983, vol. 24, No. 10, p. 1071-1074.

Allinger et al., "Conformational Analysis. LI. The Conformations of Cyclohexanone Rings in Simple Molecules", Journal of the American Chemical Society, Jul. 5, 1966, vol. 88, No. 13, p. 2999-3011.

Mohrle et al., "Heterocyclische Spirocyclohexadienone aus substituierten Phenolen", Z. Naturforsch, 1995, 50b, p. 1859-1868.

Traubenberg, "On the Question of the Condensation of Phenol With Formaldehyde", Angew. Chem., vol. 36, p. 515, dated 1923 (with English Translation).

Roger James et al., "Synthesis, Biological Evaluation, and Preliminary Structure-Activity Considerations of a Series of Alkylphenols as Intravenous Anesthetic Agents", J. Med. Chem., vol. 23, pp. 1350-1357, dated 1980.

R.V. Ramanamma et al., "Synthesis of three naturally occurring diisopropylmethylphenols", Indian Journal of Chemistry, vol. 28B, pp. 517-519, dated Jun. 1989.

E.E. van Tamelen et al., Biogenetic-Type Total Synthesis of (±)-Triptonide and (±)-Triptolide, J. Am. Chem. Soc., vol. 104, pp. 1785-1786, dated 1982.

David R. Armstrong et al., "Oxidative Coupling of Phenols. Part 6[1]. A Study of the Role of Spin Density Factors on the Product Composition in the Oxidations of 3,5-Dimethylphenol and Phenol", J. Chem. Soc. Perkin Trans. II, pp. 563-568, dated 1983.

Puttnam: The Infrared Vibrations of a s-Butyl, J. Chem. Society (London), pp. 2934-2937, dated 1960.

Ryohel Nakane et al., Tertiary Butylation at Low Temperatures, Contribution from the Institute of Physical and Chemical Research, Tolyo, Japan, p. 3011, dated Nov. 16, 1965.

J.M. Sendra et al., Volatile Constituents of Spanish Origanum (*Coridothymus capitatus*) Essential Oil, Phytochemistry, vol. 19, pp. 89-92, dated 1980.

H. Mohrle, et al., "Heterocyclic Spirocyclohexadienones from Substituted Phenols", Journal for Natural Research, vol. 50b, pp. 1859-1868, dated 1995, (with English Translation).

Ya. B. Kozlikovskii et al., Condensation of Phenol with Aldehydes in the Presence of Aluminum Phenolate, Zhurnal organicheskoi khimii, vol. 21, No. 11, pp. 2403-2407, dated 1985 (with English Translation).

F. J. Sowa et al., Organic Reactions With Boron Fluoride. V. The Rearrangement of Isopropylphenol, o-, m- and p-Cresyl Ethers, Department of Chemistry, University of Notre Dame, vol. 55, pp. 3402-3407, dated Aug. 5, 1933.

Balough et al., Oxidations With Silver Carbonate/Celite. V. Oxidations of Phenols and Related Compounds, J. Org. Chem., vol. 36, No. 10, pp. 1339-1341, dated 1971.

Benjamin Blank, et al., Isopropyl Analogs of Thyroid Hormones, Thyromimetics, vol. VII, pp. 653-656, dated Jul. 1967.

Jacques Bassus, et al., XI.—Comparison between theoretical and experimental reactivities of methyl-4 phenol during isopropylation reactions. Physiocochemial study of compounds obtained., Physicochemical Study of Phenols, No. 595, pp. 3031-3033, dated 1974 (with English Translation).

Ji. C. Xapuehko et al., Ukrainian Chemical Journal, Organic Chemistry, Alkylation of n-Cresol With Propylene In The Presence of BF$_3$ H$_3$PO$_4$ and BF$_3$ . O(C$_2$H$_5$)2, vol. XXX, No. 2, pp. 187-190, dated 1964 (with English Translation).

J. Petranek et al., "One-Electron Oxidation Of 2,6-Dialkyl-4-Alkoxyphenols; Effect Of Alkyl Substituents", Collection Czechoslov. Chem. Commun., vol. 35, pp. 830-837, dated Mar. 1970.

W. Klement et al., Pain On I.V. Injection Of Some Anaesthetic Agents Is Evoked By The Unphysiological Osmolality Or pH Of Their Formulations, British Journal of Anaesthesia, vol. 66, pp. 189-195, dated 1991.

W. Klement et al., British Journal of Anaesthesia, vol. 67, No. 4, pp. 506-507, dated Oct. 1991.

P. Pratesi, et al., "Sull'etere monoetossi-metil-fosforico", Bollettino Scientifico Della Facolta Di Chimica Industriale Di Bologna, Supplied by the British Library—"The World's Knowledge", pp. 250-251, dated 1940, with English Translation Attached.

PROCESS FOR PREPARING WATER SOLUBLE PHOSPHONOOXYMETHYL DERIVATIVES OF ALCOHOL AND PHENOL

This application claims priority to U.S. Provisional Application Ser. No. 60/341,867 filed Dec. 21, 2001, which is hereby incorporated by reference in its entirety.

FIELD OF THE INVENTION

The present invention relates to a novel process for preparing water-soluble prodrugs of aromatic hindered hydroxyl group containing pharmaceuticals. Particularly, the present invention concerns a process for making water-soluble phosphonooxymethyl ethers of hindered alcohol and phenol containing pharmaceuticals, such as camptothecin, propofol, etoposide, Vitamin E and Cyclosporin A.

BACKGROUND OF THE INVENTION

The successful delivery of a pharmaceutical to a patient is of critical importance in the treatment of disorders. However, the use of many clinical drugs with known properties is limited by their very low water solubility. As a result of low water solubility these drugs must be formulated in co-solvent pharmaceutical vehicles, including surfactants. These surfactants have been shown to lead to severe side effects in humans that limit the clinical safety of these drugs and therefore the treatment of several disorders.

For example, camptothecin is a natural product isolated from barks of the Chinese camptotheca tree, Camptotheca accuminata. It has been shown to have strong anti-tumor activity in several in vivo animal models including major tumor types such as lung, breast, ovary, pancreas, colon and stomach cancer and malignant melanoma. The serious drawback of camptothecin is its very limited water solubility. For biological studies it is necessary to dissolve the compound in a strong organic solvent (DMSO) or to formulate the drug as a suspension in Tween 80:saline, which is an undesirable drug formulation for human therapy. Recently two analogs of camptothecin with moderate water solubility have been approved in United States for treatment of advanced ovarian cancer (Hycamtin) and colorectal cancer (Camptosar).

Other drugs, like camptothecin, that have similar problems are cyclosporin A (CsA), propofol, etoposide and Vitamin E (alpha-tocopherol). Like camptothecin, CsA has within its structure a sterically hindered alcohol, a secondary alcohol in this case. CsA is formulated in a CremophorEL/ethanol mixture.

An example of a sterically hindered, poorly water-soluble phenol is propofol, an anesthetic. Propofol is formulated for i.v. clinical use as a o/w emulsion. Not only is propofol poorly water soluble, but it also causes pain at the site of injection. The pain must be ameliorated such as with lidocaine. Moreover, because the Propofol is formulated as an emulsion, it is difficult and questionable to add other drugs to the formulation and physical changes to the formulation such as an increase in oil droplet size can lead to lung embolisms, etc.

U.S. Pat. No. 6,204,257 describes a water-soluble form of alcohol and phenol containing drugs such as camptothecin and propofol. With respect to camptothecin, compounds are phosphonooxymethyl ethers of camptothecin in the form of the free acid and pharmaceutically acceptable salts thereof. The water solubility of the acid and the salts facilitates preparation of pharmaceutical formulations.

However, the methods of making the water-soluble form of alcohol and phenol containing drugs described in U.S. Pat. No. 6,204,257 are complicated and utilize expensive and carcinogenic reagents. For instance, the synthesis of O-phosphonooxymethylpropofol requires 6 steps as summarized in the reaction scheme below.

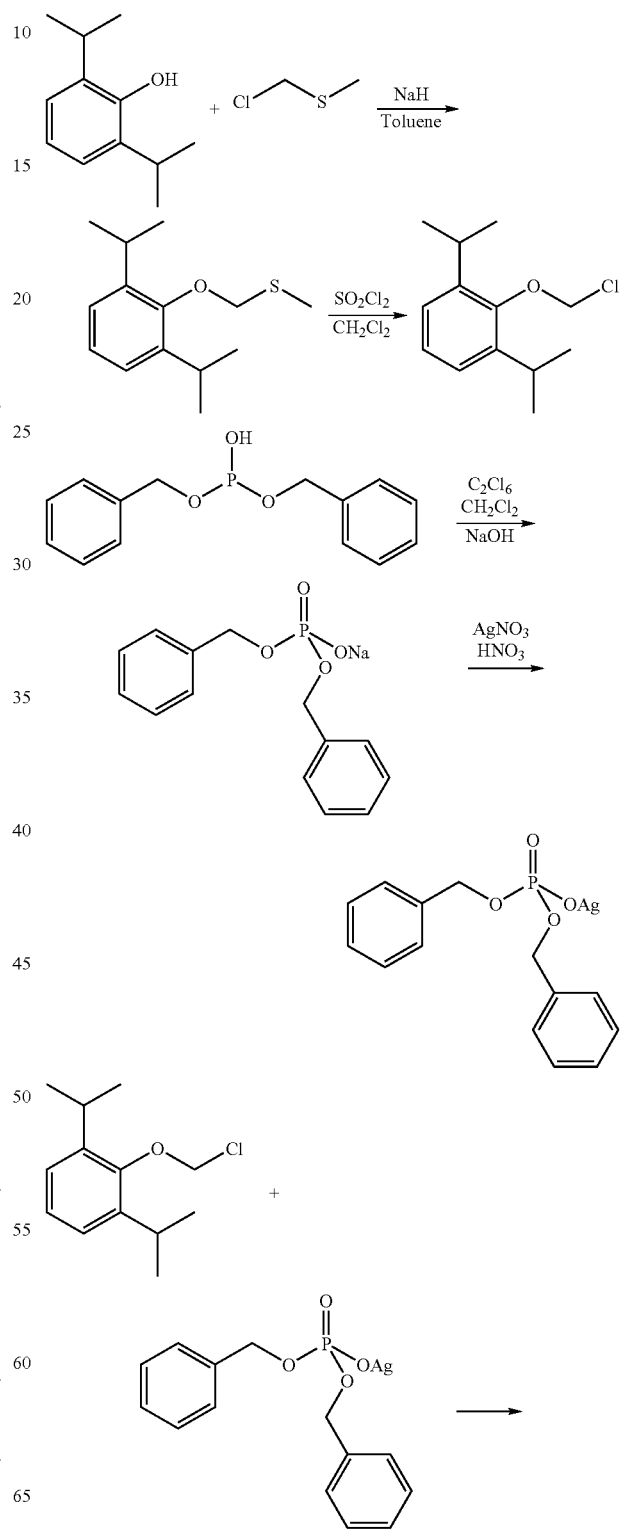

-continued

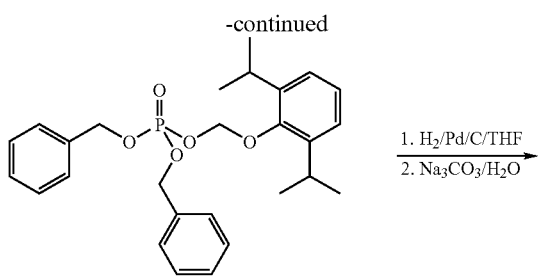

1. H₂/Pd/C/THF
2. Na₃CO₃/H₂O

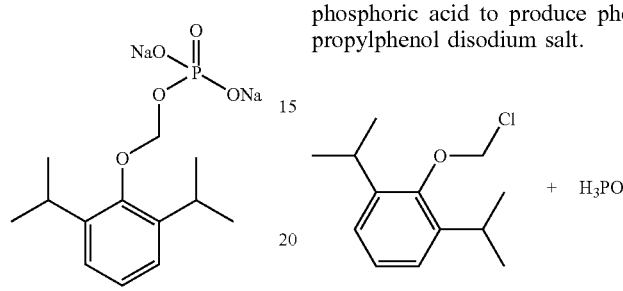

It is desirable to have a process that is shorter and does not use carcinogenic or expensive reagents.

BRIEF SUMMARY OF THE INVENTION

The present invention relates to a new process of preparing water-soluble phosphonooxymethyl derivatives of alcohol- and phenol-containing drugs, in particular phosphono-O-methyl 2,6-diisopropylphenol disodium salt.

The present invention is particularly directed to preparing water-soluble phosphonooxymethyl derivatives comprising the steps of:

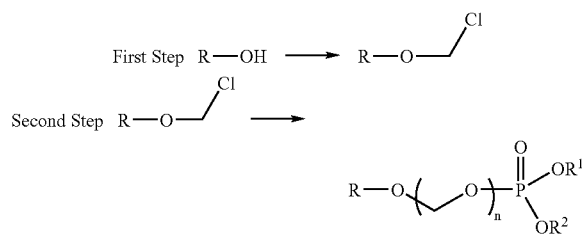

wherein R—OH represents an alcohol- or phenol-containing drug, n represents an integer of 1 or 2, $R^1$ is hydrogen, an alkali metal ion, or a pharmaceutically acceptable cation, and $R^2$ is hydrogen, an alkali metal ion, or a pharmaceutically acceptable cation.

In a preferred embodiment, 2,6-diisopropylphenol is reacted with bromochloromethane to produce O-chloromethyl-diisopropylphenol.

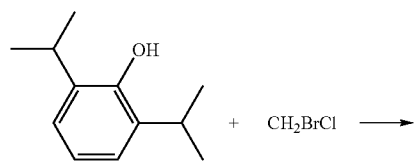 + CH₂BrCl ⟶

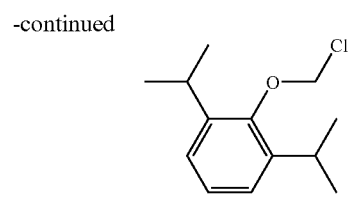

The O-chloromethyl-diisopropylphenol is reacted with phosphoric acid to produce phosphono-O-methyl 2,6-isopropylphenol disodium salt.

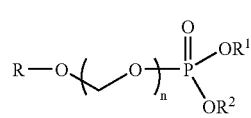 + H₃PO₄ ⟶

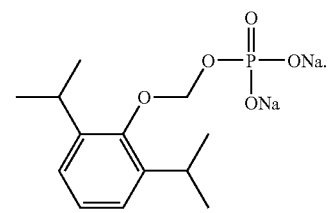

DETAILED DESCRIPTION OF THE INVENTION

The present invention relates to a new process of preparing water-soluble phosphonooxymethyl derivatives of alcohol- and phenol-containing drug, in particular phosphono-O-methyl 2,6-diisopropylphenol disodium salt. Such phosphonooxynethyl derivatives are described in U.S. Pat. No. 6,204,257, which is hereby incorporated by reference in its entirety. The process of the present invention requires only two steps and does not require the carcinogenic and expensive raw materials of the prior art processes. Moreover, chromatography is not required. The process results in high product yields of product of up to 85%, typically about 40 to 85%.

The invention described herein involves a new process for preparing water soluble phosphonooxymethyl derivatives of alcohol and phenol containing pharmaceuticals represented by formula I:

$$R-O\left(O\right)_n\overset{\overset{O}{\|}}{P}\overset{OR^1}{\underset{OR^2}{}}$$  I Formula I is the derivative of ROH, wherein ROH represents an alcohol- or phenol-containing drug, such as camptothecin, propofol, etoposide, vitamin E and cyclosporin A. ROH is preferably a phenol-containing pharmaceutical, such as propofol. Also included are some drugs for which injectable forms are not possible due to their inherent poor water solubility. These include, but are not limited to, danazol, methyltestosterone, iodoquinol, atovaquone, and fluconale.

The term n represents an integer of 1 or 2, preferably 1. $R^1$ is hydrogen or an alkali metal ion including sodium, potassium or lithium or a protonated amine or protonated amino acid or any other pharmaceutically acceptable cation. $R^2$ is hydrogen or an alkali metal ion including sodium, potassium or lithium or a protonated amine or a protonated amino acid or any other pharmaceutically acceptable cation.

The derivatives according to formula I can be prepared in accordance with the following reaction scheme:

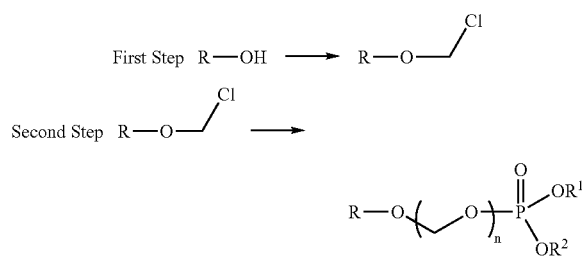

wherein R—OH represents an alcohol- or phenol-containing drug, n represents an integer of 1 or 2, $R^1$ is hydrogen, an alkali metal ion, or a pharmaceutically acceptable cation, and $R^2$ is hydrogen, an alkali metal ion, or a pharmaceutically acceptable cation.

In a first step R—OH is reacted with a large excess of bromochloromethane in the presence of a base and tetrahydrofuran (THF). The resulting product is then reacted with an excess of phosphoric acid and a base in a suitable solvent.

An example of the above scheme can be illustrated using 2,6-diisopropylphenol as a starting material. In the first step, 2,6-diisopropylphenol is reacted with bromochloromethane to produce O-chloromethyl-diisopropylphenol.

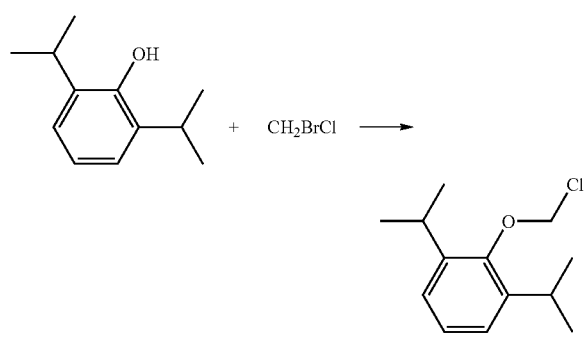

In the second step, the O-chloromethyl-diisopropylphenol is reacted with phosphoric acid to produce phosphono-O-methyl 2,6-diisopropylphenol disodium salt.

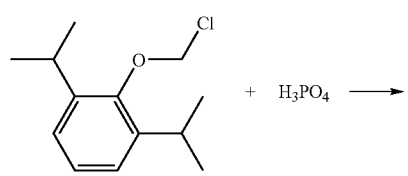

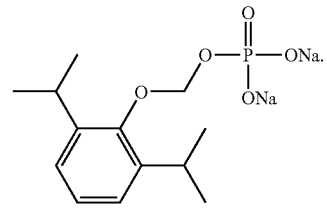

More specifically, in the first step, 2,6-diisopropylphenol is reacted with a large molar excess of bromochloromethane in the presence of a base and a suitable solvent, preferably tetrahydrofuran (THF), to yield O-chloromethyl-2,6-diisopropylphenol. The reaction temperature may be about 20° C. to about 100° C., preferably about 25° C. to about 65° C.

The base is preferably an alkali metal hydroxide or alkali metal hydride. Suitable alkali metal hydroxides and hydrides include, but are not limited to, sodium hydride and sodium hydroxide.

The amount of base is at least about 1.5 moles of base to 1 mole 2,6-diisopropylphenol. The amount of bromochloromethane is at least about 10 moles, preferably about 10 to about 30 moles, of bromochloromethane to 1 mole 2,6-diisopropylphenol. It is contemplated that bromochloromethane may be substituted with iodochloromethane.

THF may be substituted with other appropriate solvents such as non-protic oxygen containing solvents with strong dissolution power such as glycol ethers.

In a second step, the O-chloromethyl-2,6-diisopropylphenol is reacted with a molar excess of phosphoric acid and a base in a suitable solvent. At least about 3, preferably about 3 to about 10, typically about 6, moles of phosphoric acid and base are combined with 1 mole of O-chloromethyl-2,6-diisopropylphenol. The reaction temperature is below 100° C., typically about 25° C. to about 80° C.

Suitable solvents include polar aprotic solvents such as acetonitrile, dimethylformamide (DMF), dimethylsulfoxide (DMSO), or N-methylpyrrolidone (NMP). The solvent should be capable of solubilizing the triethylammonium salt of the product. The base is preferably an alkylamine or pyridine or a substituted pyridine derivative. More preferably, the base is triethylamine The solvent is then removed and the residue is dissolved in water and acidified with, for example HCl, to a pH of about 1 to about 2, preferably about 1.5. The product in its free acid form is extracted into MTBE.

The solvent is then removed such as in vacuo. The residue is dissolved in water, the pH is adjusted to about 8 to about 11.5 with a suitable reagent, for example NaOH, and the solution is extracted with a suitable solvent such as toluene. The solution may then be concentrated. Isopropanol or other suitable solvent may be added and then the product precipitated or recrystallized. Suitable solvents include polar, water miscible organic solvents such as acetone, acetonitrile, an alcohol, THF, or dioxane to yield phosphono-O-methyl 2,6diisopropylphenol disodium salt.

EXAMPLE 1

Step 1: A four-necked 500 mL round bottom flask was equipped with a mechanical stirrer, nitrogen inlet, condenser and thermometer. It was charged with 17.8 grams (0.10 moles) of 2,6-diisopropylphenol, 200 mL of THF, 8.0 grams (0.20 mole) of sodium hydroxide pellets, and 387 grams (3.0 moles, 194 mL) of bromochloromethane. The reaction mixture was heated to 64° C. and held for 2-3 hours until no more 2,6-diisopropylphenol was present as measured by GC. After cooling to 25° C., the suspension was filtered and the filter cake was washed with THF. The THF was removed by rotary evaporation and the resultant oil was distilled under vacuum (0-1 torr, b.p.=80° C.) to give 16.9 grams (0.074 moles, 75% yield) of O-chloromethyl 2,6-diisopropyl phenol.

Step 2: A four-necked 1 L round bottom flask, fitted with a temperature controlling thermocouple, was placed in a heating mantle. The flask was charged with 300 mL acetonitrile followed by triethylamine (48.7 mL, 0.349 mol) and 85% phosphoric acid (18.7 mL, 0.318 mol). O-chloromethyl 2,6-diisopropylphenol (12 g, 0.0529 mol) was then added and the reaction solution was heated to 65° C. for 2 h. The reaction was deemed to be complete by the disappearance of starting material as determined by TLC and HPLC. The solution was allowed to cool and the mixture was concentrated under reduced pressure. The residue was dissolved in 500 mL water and acidified with 8N HCl to pH=1.5. This solution was extracted three times with 500 mL MTBE. The combined organic extracts were washed once with brine and the organic layer was filtered through celite. To the residue was added 60 mL water and 20% NaOH solution was added to pH=8.6. This solution was washed twice with 50 mL toluene. The aqueous solution was concentrated under reduced pressure to half of the original volume, and 315 mL of isopropanol was added. The mixture was heated to 70° C. to dissolve the product then was cooled to 0° C. The white solid that crystallized was isolated by suction filtration, washed one time with 45 mL of isopropanol and was dried in the vacuum oven (30 inches Hg, 45° C.) for 48 hours to give 13.1 grams (0.039 moles, 75% yield) of a white solid.

EXAMPLE 2

Step 1: 2,6-Diisopropylphenol (20 kg, FW (formula weight)=178, 112 mol, 1 equiv.) is reacted with bromochloromethane (347 kg, FW=129, 2,682 mol, 24 equiv.) and sodium hydroxide (11 kg, FW=40, 280 mol, 2.5 equiv.) in tetrahydrofuran (108 kg, FW=72, 1,498 mol, 13.3 equiv.) at reflux for approximately 1.5 hours. After cooling to 20° C., the reaction mixture is quenched with water (87 kg). The organic layer is collected and washed with 15% sodium chloride aqueous solution (78 kg) twice. The organic layer is collected again after the layer separation, and the solvents are distilled from the organic layer to afford a crude oil. The crude oil is distilled by simple distillation to yield a purified chloromethyl(2,6-diisopropylphenyl)ether (FW=227) as a light yellow oil.

Step 2: Chloromethyl(2,6-diisopropylphenyl)ether (20 kg, FW=227, 88.20 mol, 1 equiv.) is reacted with phosphoric acid (81 kg, 85%, FW=98, 705 mol, 8 equiv.) and triethylamine (89 kg, FW=101, 883 mol, 10 equiv.) in acetonitrile (200 kg, FW=41, 4,872 mol, 55 equiv.) at approximately 75° C. for 3 hours. The reaction mixture is cooled and concentrated under vacuum. The resulting slurry is dissolved in water. The pH of the mixture is adjusted to 1.5 with concentrated hydrochloric acid. The acidified mixture is extracted twice with toluene. The two organic extracts are combined and washed with water once. The organic solution is concentrated under vacuum. The resulting oil is mixed with purified water, USP. The pH of the mixture is adjusted to 11 with 50% sodium hydroxide aqueous solution. The aqueous mixture is washed with toluene twice. The aqueous mixture is then partially concentrated under vacuum to about 40 to 50% of the original volume. Isopropyl alcohol (525 kg) is added to the concentrated aqueous solution at 70° C., then cooled to 0° C. to crystallize the product. The solid is collected by filtration and dried under vacuum to afford phosphono-O-methyl 2,6-diisopropylphenol disodium salt ($C_{13}H_{19}Na_2O_5P$, FW=332)

EXAMPLE 3

Step 1: A four-necked 500 mL round bottom flask was equipped with a mechanical stirrer, nitrogen inlet, condenser and thermometer. It was charged with 8.9 grams (0.05 moles) of 2,6-diisopropylphenol, 100 mL of THF and 4.0 grams (0.10 mole) of sodium hydroxide pellets. The resultant green suspension was heated to 60-65° C. and held for one hour. The reaction mixture was cooled to 30° C. and 100 mL (199 grams, 1.54 moles) bromochloromethane was added and heating was resumed. The reaction mixture was held at 64° C. for 2-3 hours until no more 2,6-diisopropylphenol was present as measured by GC. After cooling to 25° C., the suspension was filtered through Celite and the filter cake was washed with THF. The THF was removed by rotary evaporation and the resultant oil was distilled under vacuum (0-1 torr, b.p.=80° C.) to give 9.6 grams (0.042 moles, 85% yield) of O-chloromethyl 2,6-diisopropylphenol.

Step 2: A four-necked 1 L round bottom flask, fitted with a temperature controlling thermocouple, was placed in a heating mantle. The flask was charged with 300 mL acetonitrile followed by triethylamine (48.7 mL, 0.349 mol) and 85% phosphoric acid (18.7 mL, 0.318 mol). O-chloromethyl 2,6-diisopropylphenol (12 g, 0.0529 mol) was then added and the reaction solution was heated to 65° C. for 2 h. The reaction was deemed to be complete by the disappearance of starting material as determined by TLC and HPLC. The solution was allowed to cool and the mixture was concentrated under reduced pressure. The residue was dissolved in 500 mL water and acidified with 8N HCl to pH=1.5. This solution was extracted three times with 500 mL MTBE. The combined organic extracts were washed once with brine and the organic layer was filtered through celite. One equivalent of TEA was added and the solution was concentrated under reduced pressure. To the residue was added 60 mL water and 20% NaOH solution was added to pH=8.6. This solution was washed twice with 50 mL toluene. The aqueous solution was concentrated under reduced pressure. Water (30 ml) was added and the solution was cooled in an ice bath. Acetone (300 mL) was added dropwise. The resulting mixture was cooled in the refrigerator overnight. The mixture was then cooled in an ice bath for 1 hour, then the solids were filtered. The white solid was dried in the vacuum oven (30 inches Hg, 45° C.) for 48 hours to give 7.50 grams (0.023 moles, 43% yield) of a white solid.

EXAMPLE 4

2,6-diisopropylphenol was treated with with bromochloromethane in the presence of sodium hydroxide and THF to give an 85% yield of O-chloromethyl-2,6-diisopropylphenol, which was purified by vacuum distillation. Treatment of O-chloromethyl-2,6-diisopropylphenol with phosphoric acid and triethylamine in acetonitrile followed by solvent removal, dissolution in methanol, pH adjustment and precipitation with acetone gave an 85% yield of phosphono-O-methyl 2,6-diisopropylphenol disodium salt.

While the invention has been described with respect to specific examples including presently preferred modes of carrying out the invention, those skilled in the art will appreciate that there are numerous variations and permutations of the above described systems and techniques that fall within the spirit and scope of the invention.

What is claimed is:

1. A process for preparing water-soluble phosphonooxymethyl derivatives comprising the steps of:

First Step  R—OH  →  R—O—CH₂Cl

Second Step  R—O—CH₂Cl  →  R—O—(CH₂—O)ₙ—P(=O)(OR¹)(OR²)

wherein the R—O—CH₂Cl is reacted with a molar excess of phosphoric acid and a base in a suitable polar aprotic solvent; and wherein R—OH represents an alcohol- or phenol-containing drug, n represents an integer of 1 or 2, R¹ is hydrogen, an alkali metal ion, or a pharmaceutically acceptable cation, and R² is hydrogen, an alkali metal ion, or a pharmaceutically acceptable cation.

2. The process of claim 1 wherein R—OH represents camptothecin, propofol, etoposide, vitamin E, or cyclosporin A.

3. The process of claim 1 wherein n is 1.

4. The process of claim 1 wherein R¹ and R² are independently selected from the group consisting of hydrogen, sodium, potassium, lithium, a protonated amine, and a protonated amino acid.

5. The process of claim 1 wherein in step 1, R—OH is reacted with a molar excess of bromochloromethane in the presence of a base and a suitable solvent.

6. The process of claim 1 wherein in step 1, R—OH is reacted with a molar excess of iodochloromethane in the presence of a base and a suitable solvent.

7. The process of claim 5 wherein the base is an alkali metal hydroxide or alkali metal hydride.

8. The process of claim 7 wherein the base is sodium hydroxide or sodium hydride.

9. The process of claim 5 wherein the solvent is an aprotic or a non-protic oxygen containing solvent.

10. The process of claim 9 wherein the solvent is tetrahydrofuran.

11. The process of claim 5 wherein at least about 1.5 moles of base is present for every 1 mole of R—OH.

12. The process of claim 5 wherein at least about 10 moles of bromochloromethane is present for every one mole of R—OH.

13. The process of claim 12 wherein about 10 to about 30 moles of bromochloromethane is present for every one mole of 2,6-diisopropylphenol.

14. The process of claim 1 wherein R—OH is 2,6-diisopropylphenol.

15. The process of claim 1 wherein the reaction temperature in the first step is about 25° C. to about 65° C.

16. The process of claim 1 wherein at least about 3 moles of phosphoric acid are combined with 1 mole of R—O—CH₂Cl.

17. The process of claim 16 wherein about 3 to about 10 moles of phosphoric acid is present per mole of R—O—CH₂Cl.

18. The process of claim 1 wherein the reaction temperature in the second step is below 100° C.

19. The process of claim 18 wherein the reaction temperature is about 25° C. to about 65° C.

20. The process of claim 1 wherein the polar aprotic solvent is selected from the group consisting of acetonitrile, dimethylformamide, dimethylsulfoxide, or N-methylpyrrolidone.

21. The process of claim 1 wherein the base is an alkylamine or pyridine or a substituted pyridine derivative.

22. The process of claim 21 wherein the base is triethylamine.

23. The process of claim 1 wherein the pH of the second step is initially maintained at about 1 to about 2, and then adjusted to about 8 to about 11.5.

24. A process for preparing water-soluble phosphonooxymethyl propofol comprising reacting 2,6-diisopropylphenol with bromochloromethane to produce O-chloromethyl-diisopropylphenol:

2,6-diisopropylphenol + CH₂BrCl → O-chloromethyl-2,6-diisopropylphenol then reacting the O-chloromethyl-diisopropylphenol with phosphoric acid to produce phosphono-O-methyl 2,6-diisopropylphenol disodium salt O-chloromethyl-2,6-diisopropylphenol + H₃PO₄ → phosphono-O-methyl 2,6-diisopropylphenol disodium salt.

25. The process of claim 6 wherein at least about 10 moles of iodochloromethane is present for every one mole of R—OH.

26. The process of claim 25 wherein about 10 to about 30 moles of iodochloromethane is present for every one mole of 2,6-diisopropylphenol.

* * * * *